United States Patent [19]

Matthiessen

[11] Patent Number: 4,499,423

[45] Date of Patent: Feb. 12, 1985

[54] CIRCUIT ARRANGEMENT FOR CORRECTION OF A SENSOR OUTPUT

[75] Inventor: Hans Matthiessen, Gross Parin, Fed. Rep. of Germany

[73] Assignee: Drägerwerk Aktiengesellschaft, Fed. Rep. of Germany

[21] Appl. No.: 328,506

[22] Filed: Dec. 8, 1981

[30] Foreign Application Priority Data

Dec. 18, 1980 [DE] Fed. Rep. of Germany ....... 3047782

[51] Int. Cl.³ ............................................ G01N 27/42
[52] U.S. Cl. ................................... 324/425; 204/406; 324/71.1
[58] Field of Search ........................ 307/492; 328/145; 324/425, 438, 439, 71.1, 132, 140 R, 166, 225; 364/573, 571; 204/406, 432; 73/23, 29

[56] References Cited

U.S. PATENT DOCUMENTS 3,720,813  3/1973  Badessa ........................ 324/140 R
3,842,345  10/1974 Padgitt et al. ..................... 324/71.1
4,002,977  1/1977  Sun et al. ............................ 328/145
4,149,120  4/1979  Richter .............................. 324/132
4,201,906  5/1980  Puschner ....................... 219/130.33
4,217,651  8/1980  Pickering ........................... 364/571
4,247,818  1/1981  Hiroshima et al. ................ 324/225

Primary Examiner—Stewart J. Levy
Assistant Examiner—Kevin D. O'Shea
Attorney, Agent, or Firm—McGlew and Tuttle

[57] ABSTRACT

A circuit arrangement is disclosed for correcting the output of a sensor which experiences changes in sensitivity due to the presence of one or more influencing factors, such as the concentration of a material to be sensed, or the passage of time. The circuit arrangement includes a correction network which generates a simulated sensitivity curve which simulated curve is combined with the output of the signal to produce a corrected output signal which has apparent constant sensitivity.

5 Claims, 4 Drawing Figures

CIRCUIT ARRANGEMENT FOR CORRECTION OF A SENSOR OUTPUT

FIELD AND BACKGROUND OF THE INVENTION

The present invention relates to a circuit arrangement for the correction of a sensor output quantity. According to the invention, sensitivity changes of the sensor which effect the measurement result, are compensated, at least approximately, by electric circuit elements.

Electro-chemical measuring sensors, e.g. alcohol measuring cells, in which output quantities are produced on the basis of substance conversions, have in many cases, the disadvantage that the sensitivity of the sensor diminishes as a function of the concentration of the medium to be measured and its contact time. The resulting reduction in sensitivity may be caused either by an irreversible process, e.g. surface changes of the sensor, or it may be regarded, depending on the type of sensor, as a reversible fatigue process where the sensor regains its original sensitivity after some time outside the influence of the medium to be measured. In cases of electrolytic conversions which diminish the detection sensitivity of the sensor, a regeneration of the original sensor properties and hence of the original sensitivity can possibly be achieved by pole reversal.

Sensitivity changes in sensors which depend on the concentration or contact time of the medium to be measured, produce, depending on the prior history of the sensor, more or less faulty test results which must be corrected by taking into consideration the known sensitivity changes.

A circuit arrangement for the correction of sensor output quantity has been proposed in German patent application No. P 29 29 387. In this application a device is disclosed for picking up the partial pressure of gases with electrode sensors using memory data of the activity ratio between initial activity of the freshly calibrated work electrode and the activity existing at the time of measurement. This activity ratio is observed at certain intervals of time, e.g. daily. The measurement quantity is modified multiplicatively, whereby a corresponding correction of the sensitivity changes becomes possible. The measuring method described appears relatively expensive because at fixed intervals program-controlled measuring sequences must be carried out for the determination of the activity ratio.

SUMMARY OF THE INVENTION

The present invention proceeds from the problem of effecting the correction of the sensor output quantity by an electric circuit arrangement without metrological checking of the sensor at certain intervals, on the basis of a known sensitivity curve which is a function of the considered parameter quantities. The problem is solved by connecting a correction network downstream of the sensor. The correction network simulates the sensitivity curve as a function of the influence factors to be taken into consideration and produces from the sensor output quantity or from a quantity proportional thereto, a correction signal which corrects the sensor output quantity to constant sensitivity via a correction element. A sensitivity model is used, i.e., a system whose output quantity is a function of the considered influence factor and whose output quantity varies proportionally to the sensitivity of the sensor. The sensitivity model furnishes the input quantity for the correction member.

By correcting the sensor output voltage with a quantity obtained from the nominal and actual sensitivity value, a measured value with correspondingly reduced error can be obtained.

In a further development of the invention, the correction network expediently contains a digital circuit for simulation of the sensitivity curve determined at first by measurement. Analogously, logarithmic sections of the sensitivity curve can expediently be simulated by current direction-dependent R-C (resistance capacitance) members.

To generate the correction signal, a differential amplifier may advantageously be used, to whose inputs an input quantity corresponding to the sensitivity of the sensor not affected by the measured quantity and another input quantity proportional to the sensitivity of the sensor is applied, and where the amplifier output is connected with the correction element. This correction element then modifies the measured quantity in a corresponding manner.

A special application of the circuit arrangement can be found for an electro-chemical cell which is used as a sensor for determining the alcohol concentration in gas mixtures. A circuit may expediently be designed so that the sensitivity curve, at least as a function of time, and the occurring concentration values is approximately simulated in the correction network, and that the correction signal readjusts the gain of a measuring amplifier for the input quantity appearing in the circuit of the electrochemical cell as a voltage drop at a load resistance.

Accordingly, another object of the invention is to provide a circuit arrangement for correcting the output of a sensor which experiences changes in sensitivity according to a sensitivity curve, as a function of at least one influence factor, comprising a correction network which simulates the sensitivity curve as a function of the at least one influence factor, adapted to be connected to the sensor for receiving the sensor output, and for producing from the sensor output a corrected output signal of constant sensitivity.

Another object of the invention is to provide a digital circuit as the correction network.

A still further object of the invention is to provide an analog R-C circuit in the correction network.

A still further object of the invention is to provide a method of correcting the output of a signal which experiences changes in sensitivity according to a sensitivity curve comprising generating a signal simulating the sensitivity curve and combining the signal with the output of the sensor to produce a corrected output signal which has constant sensitivity.

The various features of novelty which characterize the invention are pointed with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Turning to the drawings in particular, the invention embodied therein comprises a circuit arrangement for correcting the output of a sensor which experiences changes in sensitivity, particularly an electro-chemical cell for determining alcohol concentration in a gas mixture.

Figure 1:
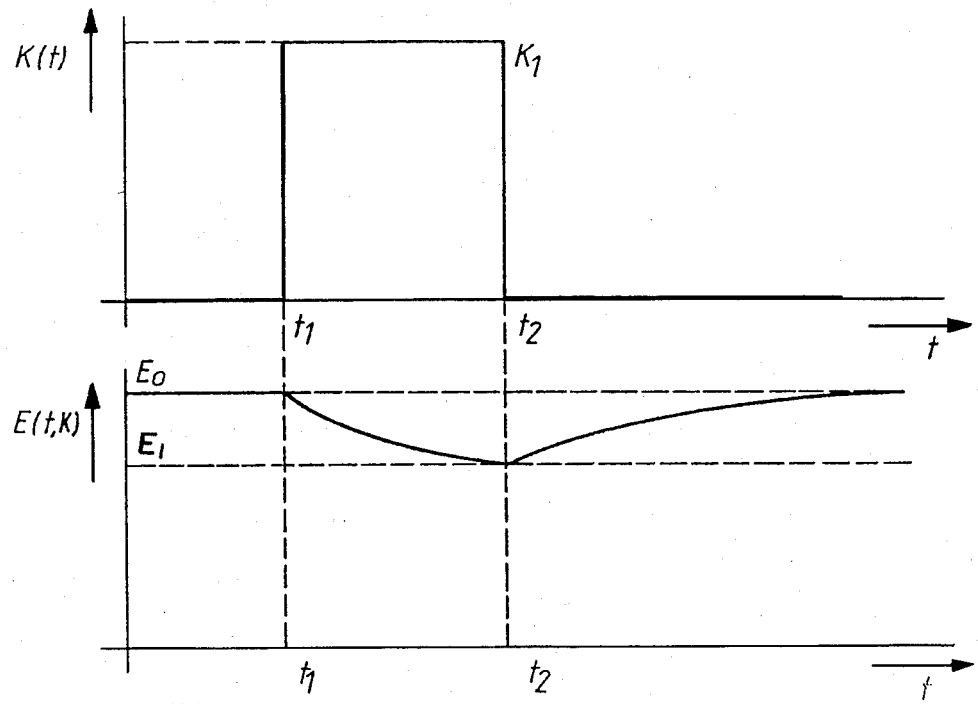
FIG. 1 is a known sensitivity curve showing sensitivity of an alcohol measuring cell plotted as a function of time and alcohol concentration.

The upper portion of FIG. 1 shows the time curve of the alcohol concentration at the alcohol measuring cell. At time $t_1$ there occurs a sudden change of the alcohol concentration from 0 to the value $K_1$, which acts up to time $t_2$. In the lower portion of FIG. 1 is shown the sensitivity curve $E(t,K)$ as a function of time and concentration. As a response to the step function (upper portion) there result two exponential branches, which must be simulated by a sensitivity model. It can be seen, for example, in the lower portion of FIG. 1 that, upon the occurrence of the step function in the upper portion of FIG. 1 which indicates the presence of a concentration $K_1$ of alcohol, the value $E_o$ outputted from the sensor drops off exponentially until it reaches the value $E_1$ at $t_2$. At this point, the concentration drops to zero and the value of the sensor output rises exponentially until eventually it will reach the initial value $E_o$ once more. The influence factor in this case is the concentration of alcohol.

Figure 2:
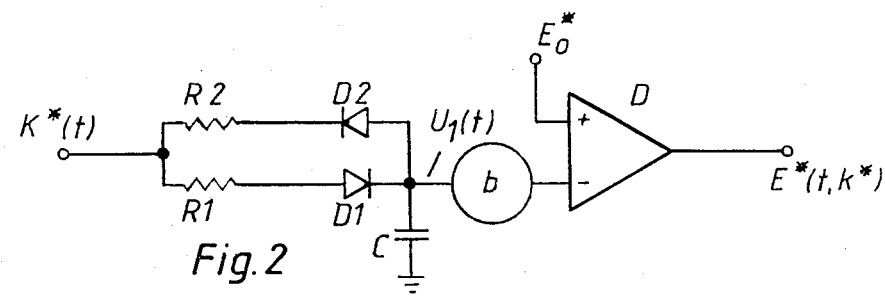
FIG. 2 is an schematic diagram of an analogous equivalent circuit used as a sensitivity model for the alcohol cell.

In FIG. 2 this is realized, in analog circuitry, via two resistances $R_1$, $R_2$ separated by diodes $D_1$, $D_2$ in connection with a capacitor C in the form of R-C elements. The input quantity is a quantity $K^*(t)$ proportional to the gas concentration at the alcohol measuring cell. The output quantity $U_1(t)$ is supplied via a final control element b, which expresses the influence factor and is approximately 0.1, to one input of a differential amplifier D. At the other input of the amplifier D, a quantity $E_o^*$ which is proportional to the sensitivity of the nonloaded alcohol measuring cell is connected. The output quantity of the differential amplifier D represents the corrected measured quantity. The curve of the correction quantity, formed as an electric additional signal here, corresponds essentially to the sensitivity curve indicated in the lower portion of FIG. 1.

Figure 3:
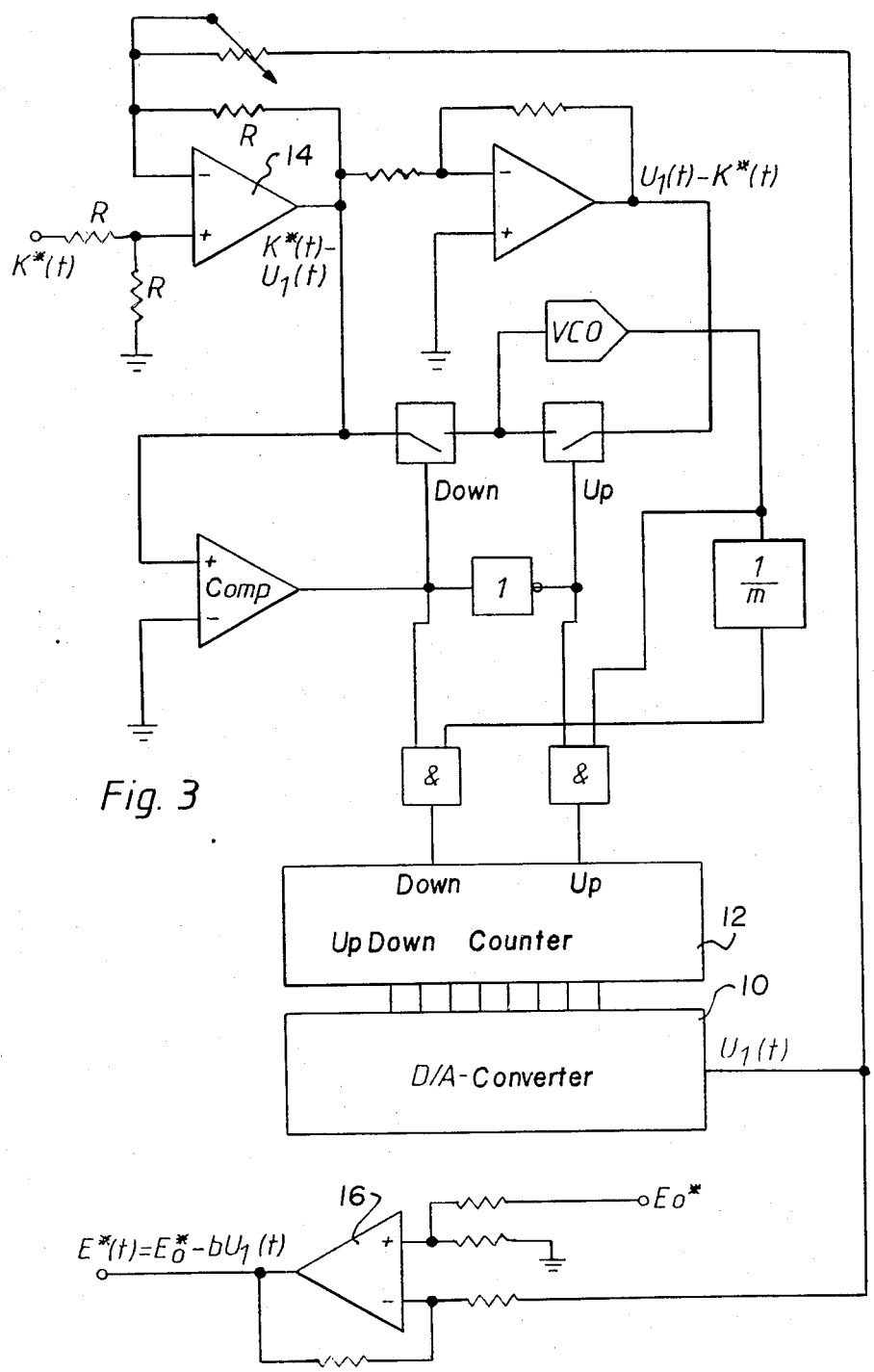
FIG. 3 is a diagram of a sensitivity model realized by a digital circuit.

In FIG. 3 is shown a sensitivity model for large time constants which are greater than or equal to one minute. This model takes the form of a digital circuit. $K^*(t)$ signifies the output quantity which is proportional to the alcohol gas concentration $K(t)$ at the alcohol measuring cell over $E_o$, i.e. the sensitivity of the measuring cell not loaded with the measured medium alcohol. $E^*(t)$ is a quantity which is proportional to the sensitivity of the measuring cell and which derives as the differences between a quantity $E_o^*$, proportional to the sensitivity of the nonloaded cell, and the product of the influence factor b and the resulting output voltage $U_1(t)$. With the stated digital circuit it is possible to realize, digitally, the analogous equivalent circuit diagram of a sensitivity model for the alcohol cell constructed by current direction-dependent R-C elements. In the digital circuit, the analogous R-C elements are replaced by counting units 12 which are transformed into an analogous quantity $U_1(t)$ again, in a D/A converter 10.

The output quantity $E^*(t)$ of the sensitivity model is then entered in a corresponding correction network by means of which the measuring cell output quantity M(t) is corrected to a value which corresponds to the true value of the measured quantity.

Figure 4:
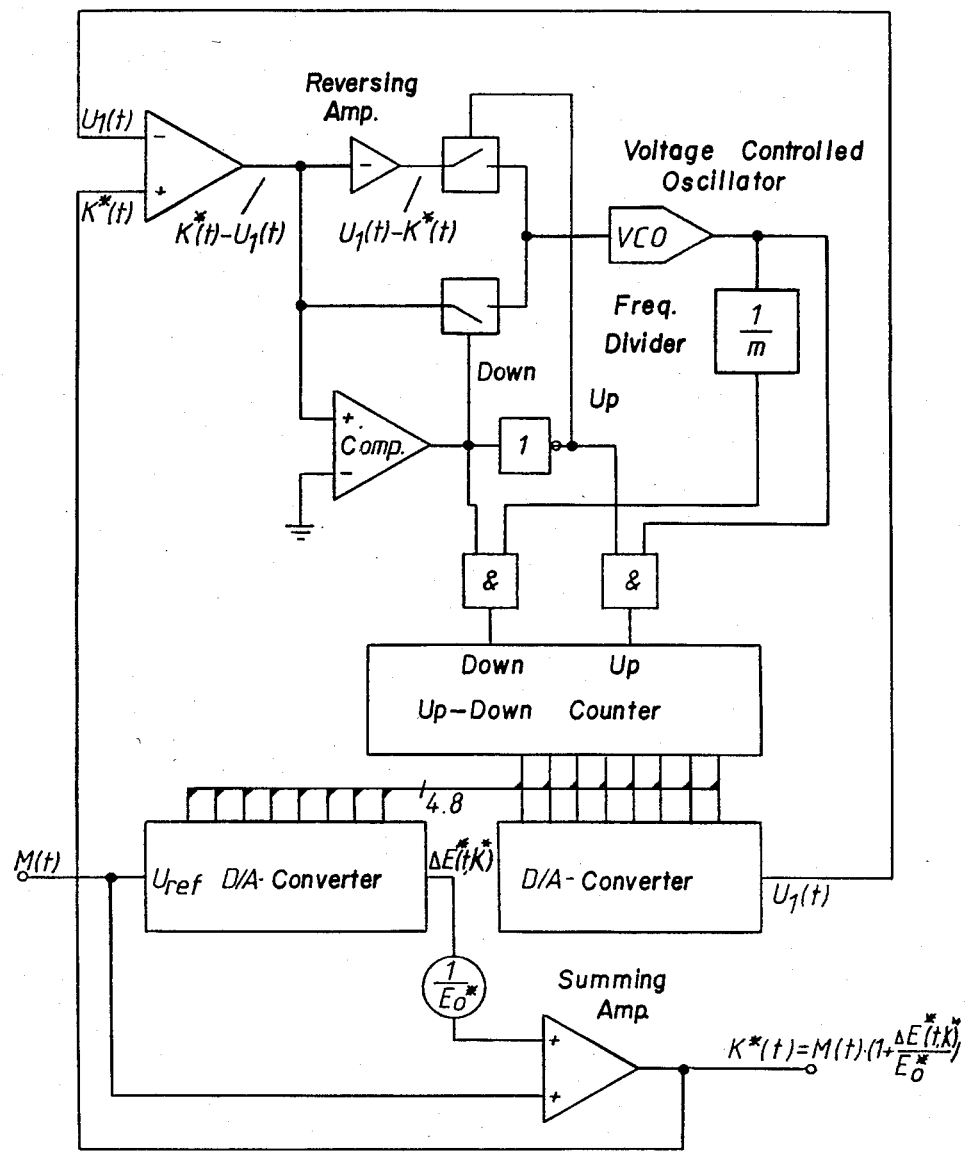
FIG. 4 is a diagram of a combination of the digital sensitivity model of the alcohol measuring cell in a correction network.

The connection of a digital sensitivity model according to FIG. 3 with a corresponding network is shown in FIG. 4. What is involved here is a favorable combination of the digital sensitivity model with a correction network. The output quantity $K^*(t)$, which is proportional to the gas concentration $K(t)$ at the measuring cell, is represented as $$M(t) \times \left[1 + \frac{\Delta E^*(t,K^*)}{E_o^*}\right].$$

The input quantity of the circuit is the electrical output quantity M(t) of the measuring cell. As output quantity of the correction network there is furnished $K^*(t)$, i.e., an electrical quantity proportional to the gas concentration at the measuring cell and corrected in consideration of the sensitivity changes of the alcohol measuring cell, e.g. a voltage.

Returning now to FIG. 3, the ditital to analog converter 10 produces an analogous signal $U_1(t)$ which is fed as an input to two difference amplifiers 14 and 16 respectively. The amplifier 14 also receives the value $K^*(t)$, as used as feedback to produce the changing value $U_1(t)$. The amplifier 16 is utilized to combine the value $U_1(t)$ with the unloaded sensitivity value $E_o^*$ (or a value proportional to the unloaded cell sensitivity value), to generate the output quantity for the sensitivity $E^*(t)$. As shown in FIG. 4, the value for $U_1(t)$ can be utilized using a frequency divider, a voltage control oscillator, suitably operated switches which are operated by the up-down counter and other components, which are shown and connected to achieve the desired result.

While specific embodiments of the invention have been shown and described in detail to illustrate the application of the principles of the invention, it will be understood that the invention may be embodied otherwise without departing from such principles.

What is claimed is:

1. A circuit arrangement for correcting the output of a sensor which experiences time dependent error changes in sensitivity, according to a sensitivity curve, as a function of at least one influence factor comprising: correction circuit means which simulates the sensitivity curve as a function of time and the at least one influence factor, connected to the sensor for receiving the sensor output and for producing from the sensor output a corrected output signal of constant sensitivity, said correction circuit means comprising a differential amplifier having two inputs and an output, one of said inputs being provided with a value corresponding to a sensitivity of the sensor when it is not experiencing a load, the other input provided for receiving a quantity proportional to the sensor output as it is changed according to the sensitivity curve.

2. A circuit arrangement according to claim 1, wherein said correction circuit means includes a digital circuit for simulating the sensitivity curve.

3. A circuit arrangement according to claim 1, wherein said correction circuit means includes at least one RC element for generating a logarithmic simulated sensitivity curve which corresponds to logarithmic sections of the sensitivity curve of the sensor.

4. A circuit arrangement according to claim 1, wherein the sensor comprises an electro-chemical sensor for determining alcohol concentration in a gas mixture, the sensitivity curve changing as a function of time and an occuring concentration value of alcohol in the gas mixture, said correction circuit means including means for readjusting a gain of a measuring amplifier for receiving an input quantity occurring as a voltage drop at a load resistance in the circuit of the electro-chemical cell.

5. A method of correcting the output of a sensor which experiences a change in sensitivity that changes in time to a known extent as a function of at least one influence factor comprising:
 generating a simulated sensitivity curve which simulates the changing sensitivity with time and as a function of the at least one influence factor;
 combining a value from the sensitivity curve with an actual output value from the sensor at each point in time plotted on the curve to generate a corrected output signal; and
 providing the corrected output signal as an indicating output of the sensor.

* * * * *